United States Patent [19]

Khare et al.

[11] Patent Number: 5,304,696
[45] Date of Patent: Apr. 19, 1994

[54] PROCESS FOR OLEFIN ISOMERIZATION

[75] Inventors: Gyanesh P. Khare; Iqbal Ahmed, both of Bartlesville, Okla.

[73] Assignee: Phillips Petroleum Company, Bartlesville, Okla.

[21] Appl. No.: 47,665

[22] Filed: Apr. 15, 1993

[51] Int. Cl.$^5$ .............................. C07C 5/23; C07C 5/25
[52] U.S. Cl. ..................... 585/668; 585/664; 585/670
[58] Field of Search ................... 585/664, 668, 670

[56] References Cited

U.S. PATENT DOCUMENTS

| | | |
|---|---|---|
| 3,032,599 | 5/1962 | Holm et al. |
| 3,132,110 | 5/1964 | Hansford .................. 585/664 |
| 3,800,003 | 3/1972 | Sobel ................... 260/683.49 |
| 3,821,123 | 6/1974 | Germanas et al. .............. 585/668 |
| 3,898,179 | 8/1975 | Germanas et al. .............. 585/668 |
| 4,407,729 | 10/1983 | Schumacher et al. ............ 502/200 |
| 4,448,995 | 5/1984 | Allen ................... 564/451 |
| 4,762,608 | 8/1988 | Didchenko et al. .............. 208/89 |
| 4,918,041 | 4/1990 | Hollstein et al. .............. 502/217 |
| 4,956,519 | 9/1990 | Hollstein et al. .............. 585/751 |
| 5,059,725 | 10/1991 | Knifton et al. .............. 568/698 |
| 5,113,034 | 5/1992 | Soled et al. .............. 585/510 |
| 5,126,489 | 6/1992 | Kurek .................. 568/319 |

OTHER PUBLICATIONS

Applied Catalysis, vol. 61, pp. 1–25 (1990), "Recent Progress in Solid Superacid", Yamaguchi.

Successful Design of Catalysts, pp. 99–111 (1988), Elsevier Publishers, T. Inui, Editor, "Design of Sulfur-Promoted Solid Superacid Catalyst".

Journal of the Chemical Society Chemical Communications, 851–52 (1980), "Synthesis of Solid Superacid Catalyst with Acid Strength of $H_{10} \leq -16.04$", Hino & Arata.

J. Am. Chem. Soc. 101 (18), pp. 6439–6441 (1979), "Reactions of Butane and Isobutane Catalyzed by Zirconium Oxide treated with Sulfate Ion. Solid Superacid Catalyst", Snipes and Herriott.

*Primary Examiner*—Patrick P. Garvin
*Assistant Examiner*—E. D. Irzinski
*Attorney, Agent, or Firm*—Marianne H. Michel

[57] ABSTRACT

A process for the double bond isomerization of olefinic compounds is provided comprising contacting an olefinic compound and a sulfated zirconia catalyst.

11 Claims, No Drawings

PROCESS FOR OLEFIN ISOMERIZATION

BACKGROUND OF THE INVENTION

This invention relates to a process for the double bond isomerization of olefinic compounds.

Double bond isomerization is the shifting of the position of a double bond in an olefinic compound. Of particular interest is the isomerization of 1-olefins to 2-olefins. The 2-olefins are useful in producing alkylate products. Such alkylate products are used in blending high octane gasolines that meet current EPA regulations without the use of lead compounds.

It would therefore be desirable to develop a process for the double bond isomerization of olefinic compounds employing a catalyst exhibiting high activity, i.e. percent conversion, and high selectivity to the desired olefin. It would also be desirable that such a process could be conducted at relatively low and thus more economical temperatures.

SUMMARY OF THE INVENTION

An object of the present invention is, therefore, to provide a process for the double bond isomerization of olefinic compounds.

In accordance with this invention a process for the double bond isomerization of olefinic compounds is provided, comprising contacting at least one olefinic compound and a sulfated zirconia catalyst under conditions sufficient to produce double bond isomerization of the at least one olefinic compound.

DETAILED DESCRIPTION OF THE INVENTION

Sulfated zirconia as used herein is defined as zirconia impregnated with sulfate ion. The sulfated zirconia catalyst can be prepared by any method known in the art. Typically, sulfated zirconia can be prepared by contacting zirconia ($ZrO_2$), hydrous zirconia ($ZrO_2 \cdot xH_2O$), or zirconium hydroxide ($Zr(OH)_4$) with an aqueous sulfate solution or a compound capable of forming sulfate ion when the product is calcined.

Zirconia is commercially available from Zirconia Sales of America. Preferably the zirconia employed will be in powder form and will have a pore volume of about 0.2 to about 0.5 cc/g (measured by water intrusion at atmospheric pressure). Preferably the surface area of the zirconia powder will be about 20 to about 150 $m^2/g$ (measured by BET method using $N_2$). Preferably the particle size of the zirconia powder will be about 0.1 to about 5 microns.

In the alternative, zirconia can be prepared by calcining zirconium hydroxide or hydrous zirconium oxide. Zirconium hydroxide can be precipitated from zirconium salt solutions upon the addition of a base. Typical zirconium salts which can be employed include zirconium oxychloride, zirconium nitrate, zirconium oxynitrate, zirconium sulfate, zirconium tetrachloride, and mixtures thereof. Suitable bases include but are not limited to ammonium hydroxide, sodium hydroxide, potassium hydroxide, alkylammonium hydroxides, and mixtures thereof.

Zirconium hydroxide can also be prepared by hydrolyzing a zirconium alkoxide with water to form the hydroxide precipitate. Examples of suitable zirconium alkoxides which can be employed include zirconium propoxide or zirconium butoxide.

Sulfate ion can be incorporated, for example, by immersing zirconia or zirconium hydroxide in about 0.01N to about 10N sulfuric acid, preferably 0.1N to 5N sulfuric acid. Examples of other compounds capable of providing sulfate ion include ammonium sulfate, zirconyl sulfate, alkali metal sulfates such as sodium sulfate and potassium sulfate, and mixtures thereof.

Examples of compounds capable of forming sulfate ion when calcined with zirconia or zirconium hydroxide include hydrogen sulfide, sulfur dioxide, sulfur trioxide, mercaptans, and sulfur- and halo-containing compounds, such as fluoro-sulfonic acid, sulfuryl chloride, or thionyl chloride, or mixtures thereof.

The amount of sulfate ion present can vary broadly, generally the sulfate ion will be present in an amount in the range of from about 0.5 to about 20 weight percent based on the total composition of the catalyst, and preferably from 1 to 10 weight percent.

The thus produced sulfated compound can then be dried at a temperature of from about 100° C. to about 150° C., followed by calcining, preferably in an oxidizing atmosphere such as air, at a temperature in the range of from about 300° C. to about 800° C., preferably from 350° C. to 650° C., and for a time of from about 0.5 hours to about 30 hours to produce the sulfated zirconia catalyst.

Olefinic compounds which can be employed in the double bond isomerization include mono-olefins which are normal chain olefins, branched olefins, cyclic olefinic compounds, and mixtures thereof. Generally, the olefinic compounds will contain from 4 to 30 carbon atoms, preferably from 4 to 20 carbon atoms. Most preferably the olefinic compounds are mono-olefins containing from 4 to 12 carbon atoms. Examples of suitable olefinic compounds include butenes, pentenes, hexenes, heptenes, octenes, decenes, isobutene, isopentene, 2,4,4-trimethyl-1-pentene, and mixtures thereof. The mono-olefins, 1-butene and 1-pentene, are especially preferred.

The double bond isomerization reaction can be carried out by contacting the olefinic compounds with the catalyst in the liquid phase or the gas phase, depending on the structure and molecular weight of the olefin, as well as reaction temperature and pressure employed.

The reaction conditions employed are the temperature, time, and pressure sufficient to produce double bond isomerization of the olefinic compound. Although the isomerization reaction temperature can vary over a wide range, generally it will be within the range of from about 0° C. to about 500° C., preferably from about 20° C. to about 300° C., more preferably from about 20° C. to about 250° C., and most preferably from 100° C. to 200° C. As demonstrated in a subsequent example, conversion is maximized at the lower temperature range.

The reaction pressure can vary broadly. For example, pressures between 0.1 and 500 atmospheres are suitable, although preferred pressures are between about 1 and 50 atmospheres because good conversion are obtained with readily available equipment.

The double bond isomerization reaction can be carried out batch-wise or continuously with fixed catalyst beds, slurried catalyst, fluidized beds, or by using any other conventional contacting techniques. The contact time required for the reaction can also vary widely, depending in part on the reaction temperature, pressure, and structure of the reactants employed, but generally will be within the range of from about 10 minutes to about 10 hours, preferably from 10 minutes to 5 hours.

Where the reaction is carried out in continuous fashion, it is convenient to express the reactant/catalyst contact time in terms of hourly space velocity (volume of feed per hour per volume of catalyst), i.e. gas hourly space velocity (GHSV) or liquid hourly space velocity (LHSV). When the reaction is carried out in the gas phase, the GHSV can range between about 10 to about 10,000, preferably from 20 to 5000. When the reaction is carried out in the liquid phase, the LHSV can range between about 0.1 to about 10.

If the reaction is carried out in the liquid phase, solvents or diluents for the reactants can be used. Aliphatic saturated hydrocarbons e.g., butanes, pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, e.g. nitrogen, argon, can be present. Preferably, for high product yield, the reaction is effected in the absence of significant amounts of deactivating materials such as water and oxygen.

The olefinic products of the invention have established utility including use in producing alkylate products.

The following example will serve to show the present invention in detail by way of illustration and not by way of limitation.

EXAMPLE

The example compares the relative effectiveness of a zirconia catalyst and a sulfated zirconia catalyst at various temperatures.

The zirconia catalyst was prepared by calcining Zirconia RC-100 powder in air for 3 hours at 550° C. Zirconia RC-100, was purchased form Zirconia Sales of America, Atlanta, Ga.

The sulfated zirconia catalyst was prepared by treating ground zirconia tablets with aqueous ammonium sulfate, followed by drying and calcining the product. Zirconia tablets were prepared by mixing 500 g RC-100 Zirconia powder with 400 mL of 2% by volume aqueous sulfuric acid in a Lancaster Mix-Muller for 10 minutes. The powder was then dried in air in an oven at 200° C. The powder was then ground and passed through a 30 mesh sieve and mixed with 10 g zinc stearate and sufficient water to attain a water content of 11.0%. 20% by weight Zirconia RC-100P (a densified version of RC-100 which contained 2% by weight zinc stearate, and 11.0% by weight water) was added and mixed well. The mixture was then tabletted using a Stokes BB2 tabletting machine using ⅛" punches and ⅛" dies and employing up to 180 lbs pressure. The cylindrical tablets were dried in air at 250° C. for 1 hour in a furnace. The dry tablets were calcined at 550° C. in air for 3 hours. The thus produced zirconia tablets were ground and sieved to yield 12×20 mesh size granules. The ground zirconia was impregnated with sulfate ion at room temperature by mixing 25 g of the ground zirconia with a solution of 2.76 g $(NH_4)_2SO_4$ in 6 mL of distilled water. The thus treated zirconia was dried in air at 150° C. for 2 hours and calcined in air by heating to a temperature of 600° C. over a period of 4 hours and holding the temperature at 600° C. for 16 hours to produce the sulfated zirconia catalyst. The final catalyst contained an estimated 9.4 weight percent sulfate.

Double bond isomerization runs with each of the above-described catalysts were conducted at atmospheric pressure in a quartz tube reactor, 30.5 cm×3.4 cm, which was charged with 10 cc of catalyst, flushed with $N_2$, and heated to the temperature indicated in Table 1. The weight of zirconia catalyst employed was 11.9 g and the weight of the sulfated zirconia catalyst employed was 12.1 g. The reaction was conducted under moisture-free conditions and 1-butene and nitrogen in a mole ratio of 1:4 were fed into the reactor at 2.0 LHSV when using the sulfated zirconia and at 2.5 LHSV when using the zirconia. The temperature indicated in Table 1 was maintained for 1 hour and a sample was taken for gas chromatography (GC) analysis. The conversion of 1-butene in weight percent of the 1-butene feed is represented by Conversion in Table 1. The selectivity to 2-butene in weight % of the converted feed is represented by Selectivity.

TABLE 1

| Run | Temperature °C. | Conversion wt % | Selectivity wt % |
| --- | --- | --- | --- |
| Zirconia | | | |
| 101 | 121 | 42.4 | 100 |
| 102 | 177 | 60.9 | 100 |
| 103 | 232 | 82.6 | 100 |
| 104 | 288 | 93.2 | 100 |
| Sulfated Zirconia | | | |
| 201 | 121 | 91.0 | 100 |
| 202 | 177 | 89.1 | 100 |
| 203 | 232 | 85.8 | 98 |
| 204 | 288 | 83.0 | 98 |

Table 1 demonstrates the effectiveness of sulfated zirconia as a double bond isomerization catalyst at relatively low temperatures.

That which is claimed is:

1. A process for the double bond isomerization of an olefinic compound containing 4 to 30 carbon atoms, comprising contacting the olefinic compound and a sulfated zirconia catalyst under conditions sufficient to produce double bond isomerization;
   wherein said contacting is conducted at a temperature in the range of from about 20° C. to about 250° C., and
   wherein said sulfated zirconia catalyst contains from about 0.5 to about 20 weight percent sulfate based on the total composition of the catalyst.

2. A process according to claim 1 wherein said contacting is conducted at a temperature in the range of from 100° C. to 200° C.

3. A process according to claim 1 wherein said olefinic compound contains 4 to 20 carbon atoms.

4. A process according to claim 3 wherein said olefinic compound contains 4 to 12 carbon atoms.

5. A process for the double bond isomerization of a mono-olefinic compound containing 4 to 12 carbon atoms, comprising contacting the mono-olefinic compound and a sulfated zirconia catalyst under conditions sufficient to produce double bond isomerization;
   wherein said contacting is conducted at a temperature in the range of from about 20° C. to about 250° C., and
   wherein said sulfated zirconia catalyst contains from about 0.5 to about 20 weight percent sulfate based on the total composition of the catalyst.

6. A process according to claim 5 wherein said contacting is conducted at a temperature in the range of from 100° C. to 200° C.

7. A process according to claim 5 wherein said mono-olefinic compound is 1-butene.

8. A process according to claim 5 wherein said contacting is conducted at a pressure in the range of from about 0.1 to about 500 atmospheres.

9. A process according to claim 8 wherein said contacting is conducted at a pressure in the range of from 1 to 50 atmospheres.

10. A process according to claim 1 wherein said sulfated zirconia catalyst contains from 1 to 10 weight percent sulfate based on the total composition of the catalyst.

11. A process for the double bond isomerization of an olefinic compound containing 4 to 30 carbon atoms, comprising contacting the olefinic compound and a sulfated zirconia catalyst under conditions sufficient to produce double bond isomerization;

wherein said contacting is conducted at a temperature in the range of from about 20° C. to about 250° C., and wherein said sulfated zirconia catalyst consists essentially of zirconia and sulfate and contains from about 0.5 to about 20 weight percent sulfate based on the total composition of the catalyst.

* * * * *